(12) United States Patent
Masaki et al.

(10) Patent No.: US 8,758,233 B2
(45) Date of Patent: Jun. 24, 2014

(54) ENDOSCOPE

(75) Inventors: Yutaka Masaki, Mitaka (JP); Keijiro Omoto, Hachioji (JP); Keiichi Arai, Hachioji (JP); Haruhiko Ueno, Akiruno (JP); Tsugio Okazaki, Hachioji (JP); Toshimasa Kawai, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/460,340

(22) Filed: Apr. 30, 2012

(65) Prior Publication Data

US 2012/0277534 A1   Nov. 1, 2012

Related U.S. Application Data

(63) Continuation of application No. PCT/JP2011/072257, filed on Sep. 28, 2011.

(30) Foreign Application Priority Data

Oct. 8, 2010   (JP) ................................. 2010-228527

(51) Int. Cl.
*A61B 1/00* (2006.01)

(52) U.S. Cl.
USPC .......................................... 600/147; 600/131

(58) Field of Classification Search
CPC ........... A61B 1/00121; A61B 1/00124; A61B 1/00126; A61B 1/00128
USPC ................................................. 600/131, 147
See application file for complete search history.

(56) References Cited

U.S. PATENT DOCUMENTS

| | | | | |
|---|---|---|---|---|
| 5,595,939 A | * | 1/1997 | Otake et al. | 438/51 |
| 5,644,951 A | * | 7/1997 | Hatamura | 74/89.42 |
| 5,735,861 A | * | 4/1998 | Peifer et al. | 606/139 |
| 6,007,485 A | * | 12/1999 | Koeda et al. | 600/178 |
| 7,347,816 B2 | * | 3/2008 | Niwa et al. | 600/154 |

(Continued)

FOREIGN PATENT DOCUMENTS

| JP | A-3-97429 | 4/1991 |
|---|---|---|
| JP | A-6-142030 | 5/1994 |

(Continued)

OTHER PUBLICATIONS

Dec. 17, 2012 European Search Report cited in Application No. 11830538.2.

(Continued)

*Primary Examiner* — Anhtuan T Nguyen
*Assistant Examiner* — Jae Woo
(74) *Attorney, Agent, or Firm* — Oliff PLC

(57) ABSTRACT

An endoscope includes a control method input section provided in a bending operation input unit and configured to input a control method of a bending operation, and a control method detector provided in an operation section body and configured to detect the input control method of the bending operation. The endoscope includes an activated portion provided in the bending operation input unit and configured to change its activated state in response to the bending operation in a bending operation input section, an activated state detector provided in the operation section body and configured to detect the activated state of the activated portion, and a drive member provided in the operation section body and configured to be driven in accordance with the detected control method and the detected activated state, thereby bending a bending section.

6 Claims, 9 Drawing Sheets

(56) References Cited

U.S. PATENT DOCUMENTS

| | | | |
|---|---|---|---|
| 7,582,056 B2* | 9/2009 | Noguchi et al. | 600/132 |
| 7,836,737 B2* | 11/2010 | Lin | 70/116 |
| 8,382,666 B1* | 2/2013 | Mao et al. | 600/202 |
| 8,409,080 B2* | 4/2013 | Gumbs et al. | 600/146 |
| 8,420,016 B2* | 4/2013 | Yardimci et al. | 422/128 |
| 8,449,456 B2* | 5/2013 | Ueno et al. | 600/146 |
| 2006/0287576 A1* | 12/2006 | Tsuji et al. | 600/132 |
| 2007/0185385 A1* | 8/2007 | Noguchi et al. | 600/132 |
| 2007/0232856 A1* | 10/2007 | Ueno et al. | 600/118 |
| 2008/0168814 A1* | 7/2008 | Makino | 70/490 |
| 2008/0281157 A1* | 11/2008 | Miyagi et al. | 600/132 |
| 2009/0054731 A1 | 2/2009 | Shigemori | |
| 2009/0191830 A1 | 7/2009 | Nagase | |
| 2009/0221873 A1* | 9/2009 | McGrath | 600/153 |
| 2012/0052460 A1* | 3/2012 | Gates | 433/29 |
| 2012/0277534 A1* | 11/2012 | Masaki et al. | 600/145 |
| 2013/0060087 A1* | 3/2013 | Yoshida | 600/112 |
| 2013/0141557 A1* | 6/2013 | Kawata et al. | 348/65 |
| 2013/0144125 A1* | 6/2013 | Konstorum | 600/131 |
| 2013/0184528 A1* | 7/2013 | Onuki et al. | 600/146 |

FOREIGN PATENT DOCUMENTS

| | | |
|---|---|---|
| JP | A-6-304122 | 11/1994 |
| JP | A-8-224206 | 9/1996 |
| JP | A-10-262900 | 10/1998 |
| JP | A-11-32977 | 2/1999 |
| JP | A-2000-23901 | 1/2000 |
| JP | A-2002-65575 | 3/2002 |
| JP | A-2002-291691 | 10/2002 |
| JP | A-2006-6569 | 1/2006 |
| JP | A-2007-289528 | 11/2007 |
| WO | WO 2006/038524 | 4/2006 |

OTHER PUBLICATIONS

Jan. 10, 2012 International Search Report issued in International Patent Application No. PCT/JP2011/072257 (with translation).

May 16, 2013 International Preliminary Report on Patentability issued in International Application No. PCT/JP2011/072257 (translation only).

Jan. 10, 2012 Written Opinion issued in International Application No. PCT/JP2011/072257 (translation only).

Jun. 5, 2012 Notice of Reasons for Rejection issued in Japanese Patent Application No. 2012-520406 (with translation).

* cited by examiner

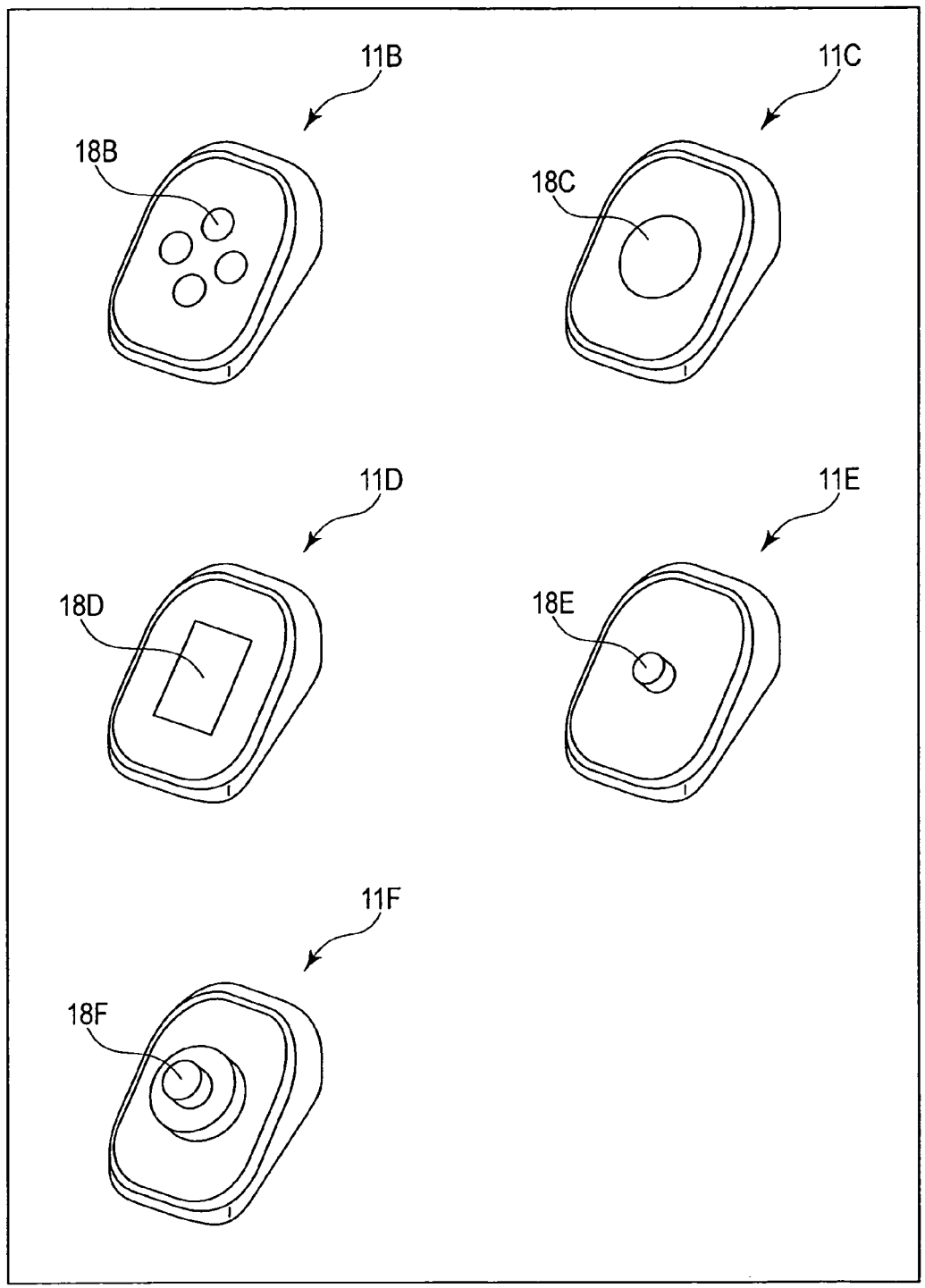
F I G. 2

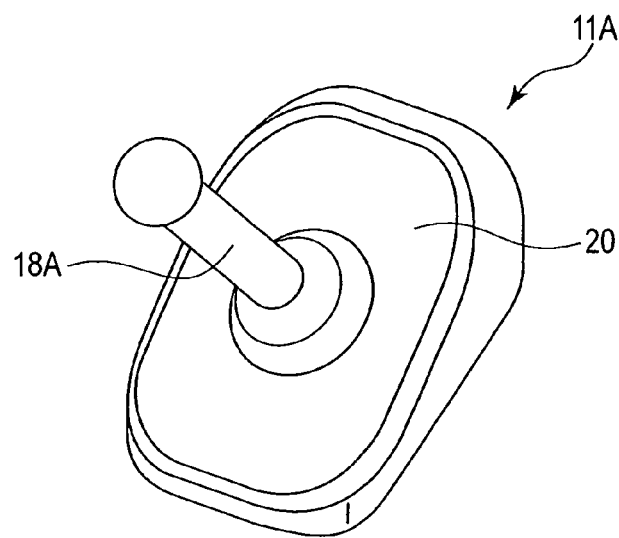
F I G. 3
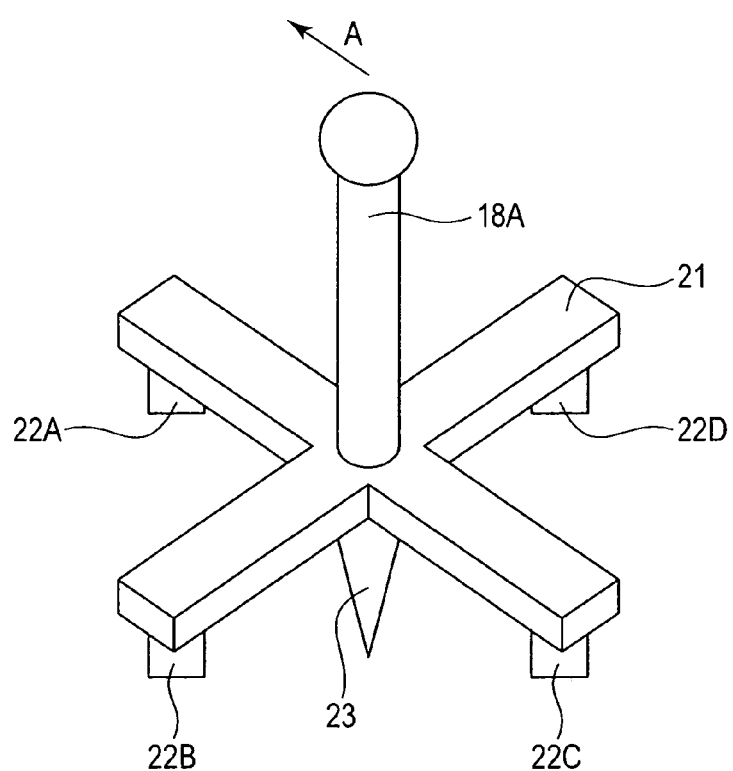
F I G. 4

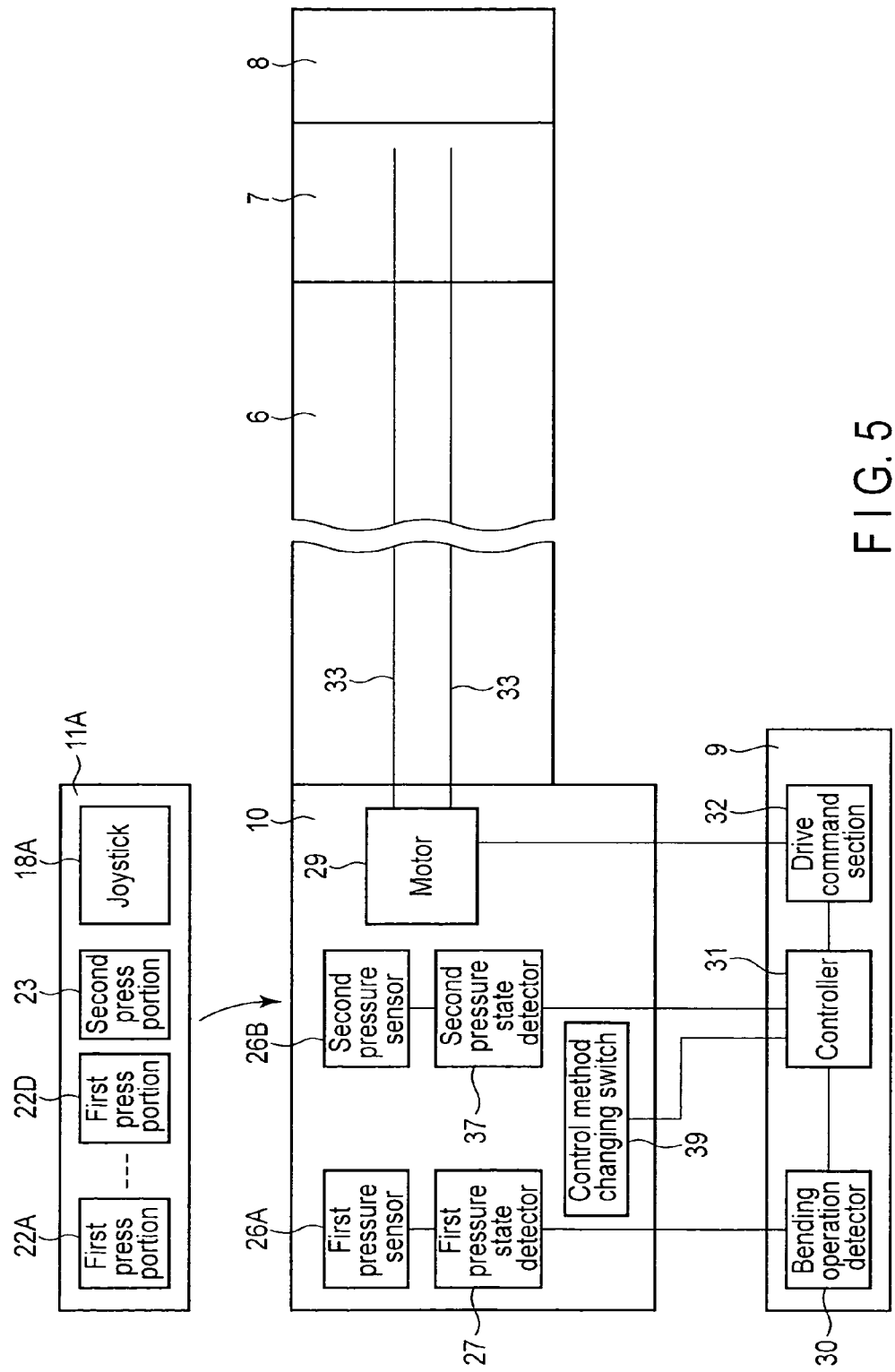
F I G. 5

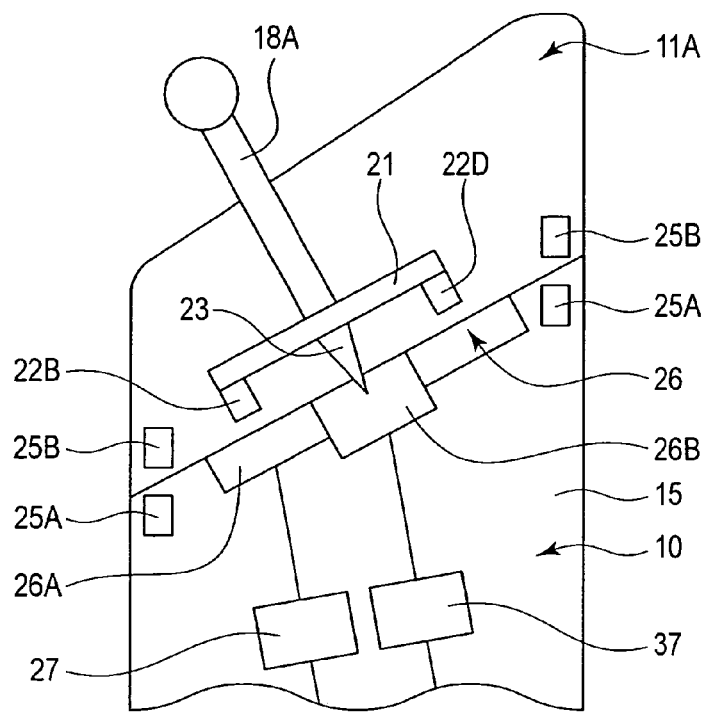
F I G. 6
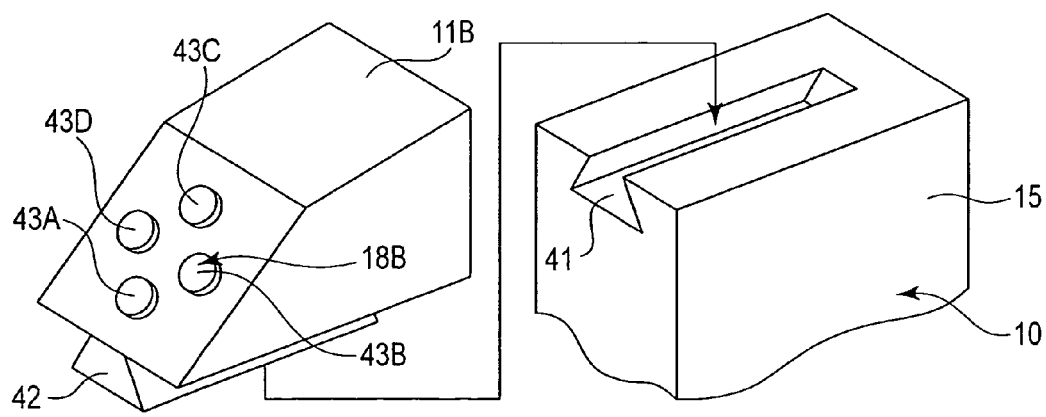
F I G. 7

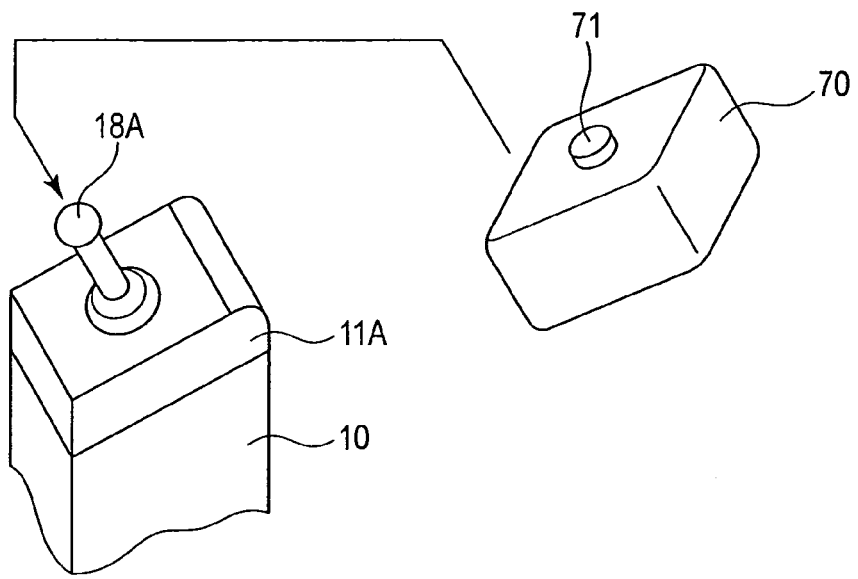
F I G. 11
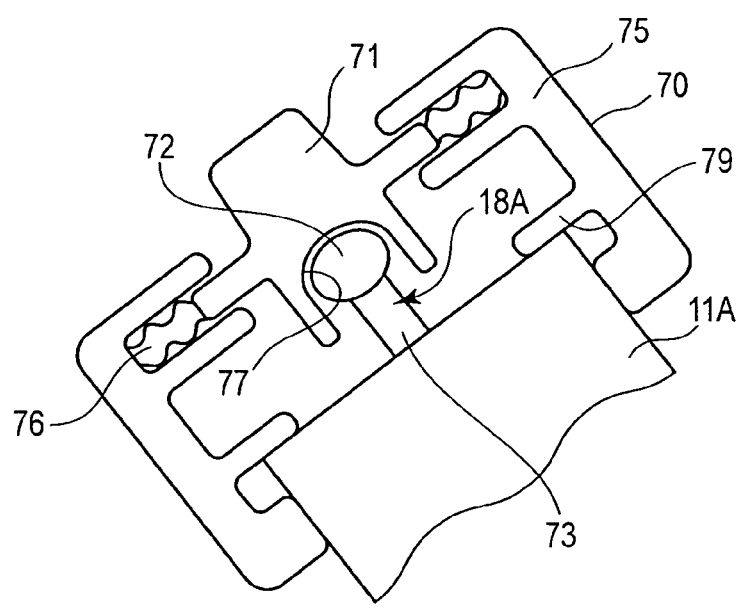
F I G. 12

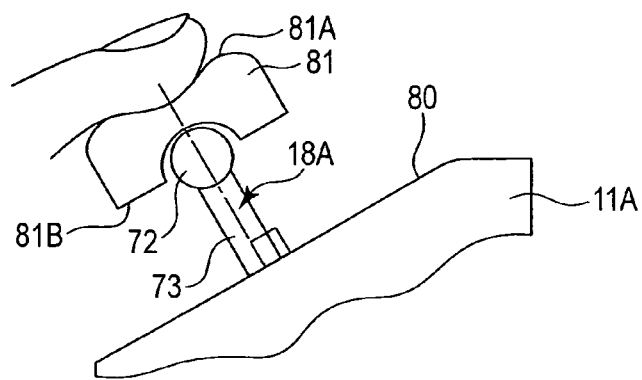
F I G. 13
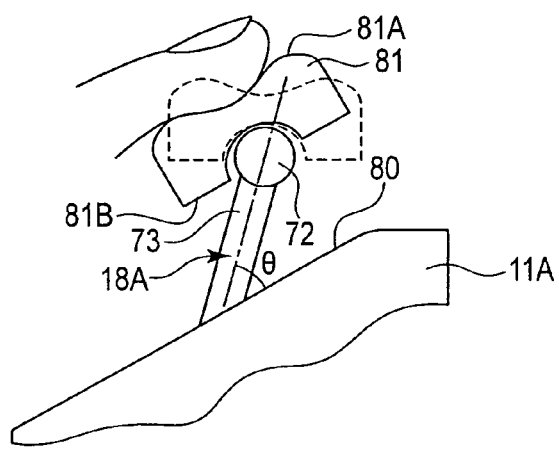
F I G. 14
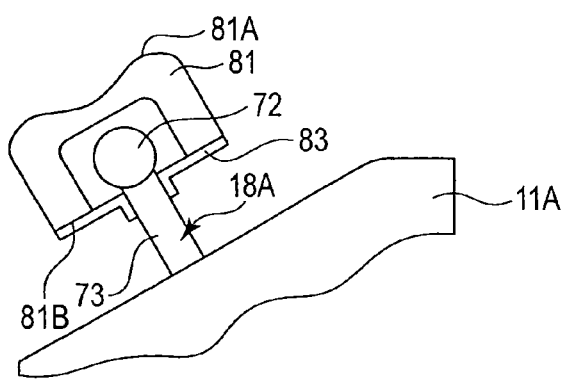
F I G. 15

ENDOSCOPE

CROSS-REFERENCE TO RELATED APPLICATIONS

This is a Continuation Application of PCT Application No. PCT/JP2011/072257, filed Sep. 28, 2011 and based upon and claiming the benefit of priority from prior Japanese Patent Application No. 2010-228527, filed Oct. 8, 2010, the entire contents of which are incorporated herein by reference.

BACKGROUND OF THE INVENTION

1. Field of the Invention

The present invention relates to an endoscope including a bending section configured to perform a bending motion by an operation in a bending operation input section.

2. Description of the Related Art

In general, an endoscope includes a bending section configured to perform a bending motion by an operation in a bending operation input section. There is known an endoscope which includes, as a bending operation mechanism configured to bend a bending section, a drive member such as a motor provided in an operation section to a proximal direction side of an insertion section. In the case of such a bending operation mechanism, the drive member is driven by the operation in a bending operation input section, and a linear member such as a wire connected to the drive member on one end moves in longitudinal directions. The other end of the linear member is connected to the bending section. In response to the movement of the linear member in the longitudinal directions, the bending section performs a bending motion.

Jpn. Pat. Appln. KOKAI Publication No. 8-224206 has disclosed an endoscope in which a bending operation switch box (bending operation input unit) including a bending operation switch that serves as a bending operation input section is removably attached to an operation section body. In this endoscope, when the bending operation switch box is attached to the operation section body, an electrical contact provided in the bending operation switch box is electrically connected to an electrical contact provided in the operation section body. Thus, by the operation in the bending operation switch, an electrical signal is transmitted to an ultrasonic motor which is a drive member provided inside the operation section body. The ultrasonic motor is driven by the transmitted electrical signal, and a bending section is bent. As the bending operation switch box is removable from the operation section body, a bending operation switch of a proper type can be used to suit each case and the preference of an operator.

BRIEF SUMMARY OF THE INVENTION

According to one aspect of the invention, an endoscope includes: an insertion section which includes a bending section configured to perform a bending motion, and which extends in longitudinal directions; an operation section body provided to a proximal direction side of the insertion section; a bending operation input unit which includes a bending operation input section configured to perform a bending operation of the bending section, and which is removably attached to the operation section body; a control method input section which is provided in the bending operation input unit, and which is configured to input a control method of the bending operation; a control method detector which is provided in the operation section body, and which is configured to detect the control method of the bending operation input by the control method input section; an activated portion which is provided in the bending operation input unit, and which is configured to change its activated state in response to the bending operation in the bending operation input section; an activated state detector which is provided in the operation section body, and which is configured to detect the activated state of the activated portion; and a drive member which is provided in the operation section body, and which is configured to be driven in accordance with the control method detected by the control method detector and the activated state detected by the activated state detector, the drive member being configured to be driven to bend the bending section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic perspective view showing various types of bending operation input units to be removably attached to an operation section body of the endoscope according to the first embodiment;

FIG. 3 is a schematic perspective view showing a first bending operation input unit of the endoscope according to the first embodiment;

FIG. 4 is a schematic perspective view showing the internal configuration of the first bending operation input unit of the endoscope according to the first embodiment;

FIG. 5 is a block diagram showing a bending operation mechanism of the endoscope according to the first embodiment;

FIG. 6 is a schematic diagram showing an attachment/removal portion between the operation section body and the first bending operation input unit in the endoscope according to the first embodiment;

FIG. 7 is a schematic perspective view showing an attachment/removal configuration between an operation section body and a second bending operation input unit in an endoscope according to a second embodiment of the present invention;

FIG. 11 is a schematic perspective view showing an operation section of an endoscope according to a second modification of the first embodiment and the second embodiment;

FIG. 12 is a schematic diagram showing an attachment/removal portion between a first bending operation input unit and an input section conversion unit in the endoscope according to the second modification;

FIG. 13 is a schematic diagram showing a first bending operation input unit of an endoscope according to a third modification of the first embodiment and the second embodiment;

FIG. 14 is a schematic diagram showing the first bending operation input unit of the endoscope according to the third modification in a state that a joystick is tilted; and FIG. 15 is a schematic diagram showing a first bending operation input unit of an endoscope according to a fourth modification of the first embodiment and the second embodiment.

DETAILED DESCRIPTION OF THE INVENTION (First Embodiment)

Figure 1:
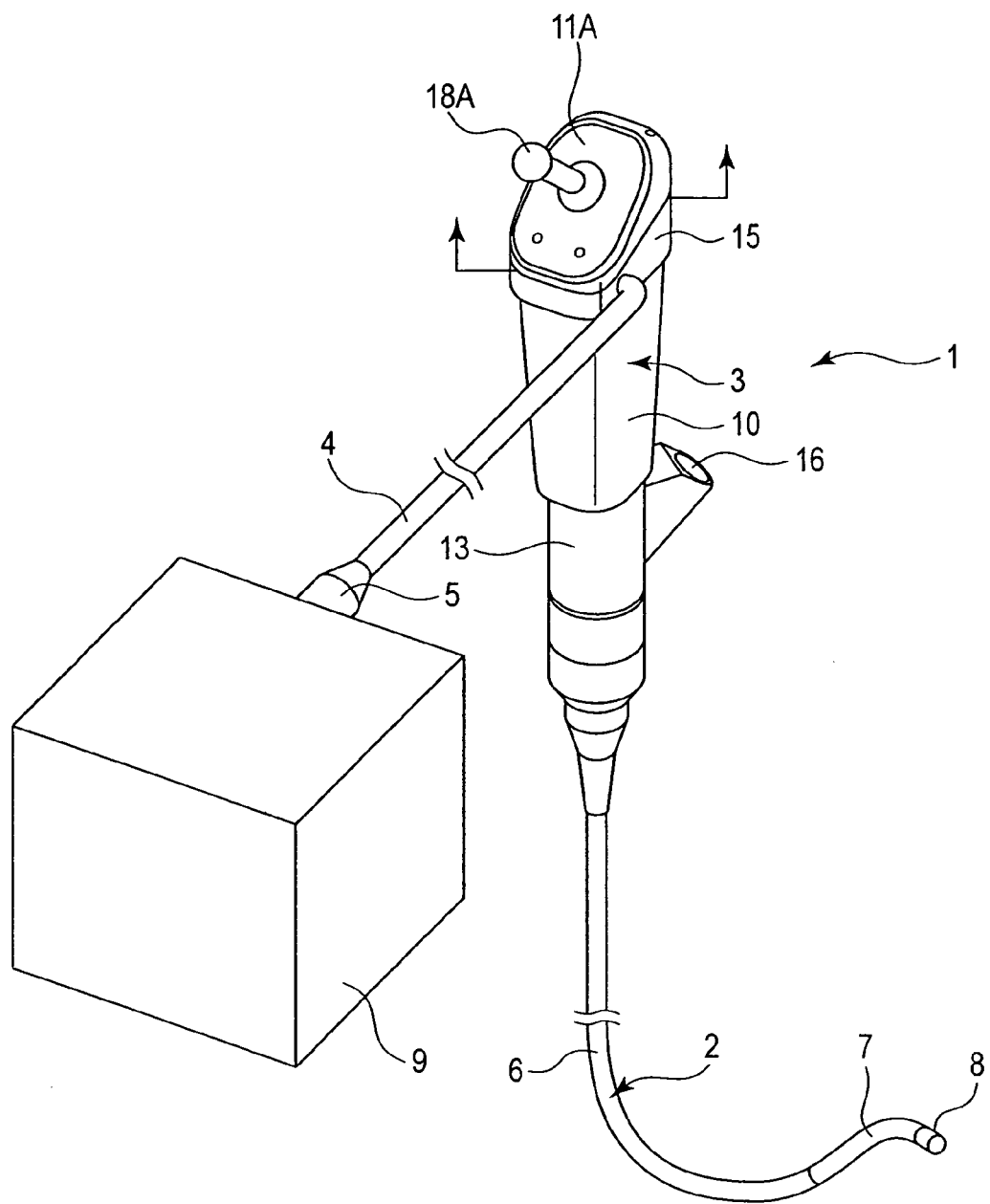
FIG. 1 is a schematic perspective view showing an endoscope according to a first embodiment of the present invention.

A first embodiment of the present invention is described with reference to FIG. 1 to FIG. 6. FIG. 1 is a diagram showing an endoscope 1 according to the present embodiment. As shown in FIG. 1, the endoscope 1 includes an insertion section 2 extending in longitudinal directions, and an operation section 3 coupled to a proximal direction side of the insertion section 2. One end of a universal cord 4 is connected to the operation section 3. A connector 5 is provided at the other end of the universal cord 4. The connector 5 is connected to a control unit 9.

The insertion section 2 includes an elongate flexible section 6 having a flexibility, a bending section 7 provided to a distal direction side of the flexible section 6, and a distal rigid section 8 provided to the distal direction side of the bending section 7. The distal rigid section 8 is provided with an imaging unit (not shown) configured to image a subject. One end of an imaging cable (not shown) is connected to the imaging unit. The other end of the imaging cable is connected to an image processing unit (not shown) through the insertion section 2, the operation section 3, and the universal cord 4 via the connector 5. Inside the insertion section 2, a light guide (not shown) extends in the longitudinal directions. One end of the light guide is connected to a light source unit (not shown) through the operation section 3 and the universal cord 4 via the connector 5. Outgoing light from the light source unit is guided by the light guide, and is applied to the subject from an illumination window (not shown) of the distal rigid section 8.

The operation section 3 includes an operation section body 10, and a first bending operation input unit 11A removably attached to the operation section body 10. The operation section body 10 includes a grip portion configured to be gripped by an operator during the use of the endoscope 1, and a unit attachment/removal portion 15 to which the first bending operation input unit 11A is attached. The operation section body 10 is provided with a treatment instrument insertion opening 16 configured to insert a treatment instrument such as forceps. Inside the insertion section 2, a treatment instrument tube (not shown) defining a treatment instrument insertion channel through which the treatment instrument is inserted extends in the longitudinal directions. One end of the treatment instrument insertion channel is in communication with the treatment instrument insertion opening 16.

The first bending operation input unit 11A includes a joystick 18A which is a bending operation input section. By tilting the joystick 18A, the bending section 7 is bent in upward/downward (UD) directions and in leftward/rightward (LR) directions. The bending operation input unit removably attached to the operation section body 10 is not exclusively the first bending operation input unit 11A which includes the joystick 18A as the bending operation input section. FIG. 2 is a diagram showing various types of bending operation input units to be removably attached to the operation section body 10. As shown in FIG. 2, a second bending operation input unit 11B includes a TACT switch (registered trademark) 18B as a bending operation input section. A third bending operation input unit 11C includes a track ball 18C as a bending operation input section. A fourth bending operation input unit 11D includes a touch pad 18D as a bending operation input section. A fifth bending operation input unit 11E includes a pointing device 18E as a bending operation input section. A sixth bending operation input unit 11F includes a jog dial 18F as a bending operation input section.

A bending operation mechanism configured to bend the bending section 7 of the endoscope 1 is described below. In the case described below, the first bending operation input unit 11A which includes the joystick 18A as the bending operation input section is attached to the operation section body 10. However, the same applies to the cases where the other bending operation input units 11B to 11F are attached to the operation section body 10 as in the case where the first bending operation input unit 11A is attached to the operation section body 10.

FIG. 3 is a diagram showing the first bending operation input unit 11A. FIG. 4 is a diagram showing the internal configuration of the first bending operation input unit 11A. As shown in FIG. 3, the first bending operation input unit 11A includes an exterior case 20. The exterior case 20 is made of a relatively soft material such as rubber or elastomer. As shown in FIG. 4, the joystick 18A which is the bending operation input portion continues to a cross-shaped base 21 inside the exterior case 20. The joystick 18A extends from the center of the base 21 to the outside of the exterior case 20. The cross-shaped base 21 is provided with four first press portions 22A to 22D protruding in a direction opposite to the joystick 18A side. Each of the first press portions 22A to 22D is provided at corresponding one of the four ends of the cross-shaped base 21. The base 21 is also provided with a second press portion 23 protruding from the center in the direction opposite to the joystick 18A side.

FIG. 5 is a diagram showing the bending operation mechanism of the endoscope 1. FIG. 6 is a diagram showing an attachment/removal portion between the operation section body 10 and the first bending operation input unit 11A in the endoscope 1. As shown in FIG. 6, the unit attachment/removal portion 15 of the operation section body 10 is provided with a first magnet 25A. The first bending operation input unit 11A is provided with a second magnet 25B. The first magnet 25A and the second magnet 25B are arranged so that attraction acts therebetween. The first bending operation input unit 11A is attached to the unit attachment/removal portion 15 of the operation section body 10 by the attraction between the first magnet 25A and the second magnet 25B.

As shown in FIG. 6, the unit attachment/removal portion 15 of the operation section body 10 is provided with a pressure sensitive sheet 26. The surface of the unit attachment/removal portion 15 to be attached to or removed from the first bending operation input unit 11A is formed into a flat shape by the pressure sensitive sheet 26. The pressure sensitive sheet 26 includes a doughnut-shaped first pressure sensor 26A, and a second pressure sensor 26B provided inside the first pressure sensor 26A.

In a neutral state in which the joystick 18A is not tilted, the first press portions 22A to 22D are out of contact with the first pressure sensor 26A, and none of the first press portions 22A to 22D press the first pressure sensor 26A. If the joystick 18A is tilted by the operator, one of the first press portions 22A to 22D located on a tilting direction side of the joystick 18A presses the first pressure sensor 26A. For example, when the joystick 18A is tilted in a direction of an arrow A in FIG. 4, the first press portion 22A presses the first pressure sensor 26A. In response to the tilting operation of the joystick 18A, each of the first press portions 22A to 22D changes its activated state between a non-press state of not pressing the first pressure sensor 26A and a press state of pressing the first pressure sensor 26A. That is, each of the first press portions 22A to 22D serves as an activated portion configured to change its activated state in response to the operation in the joystick 18A which is the bending operation input section.

As shown in FIG. 5 and FIG. 6, the first pressure sensor 26A is electrically connected to a first pressure state detector 27 provided in the operation section body 10. The first pressure state detector 27 is configured to detect the pressure state of the first pressure sensor 26A of the pressure sensitive sheet 26. The activated state of each of the first press portions 22A to 22D is detected from the pressure state of the first pressure sensor 26A. For example, when the first press portion 22A is in the press state, pressure is higher in a part of the first pressure sensor 26A pressed by the first press portion 22A than in other parts. As described above, the first pressure sensor 26A and the first pressure state detector 27 serve as activated state detectors configured to detect the activated states of the first press portions 22A to 22D which are the activated portions.

Here, no electrical contact is provided between the first pressure sensor 26A and the first press portions 22A to 22D. Therefore, the first press portions 22A to 22D which are the activated portions are electrically insulated from the first pressure sensor 26A and the first pressure state detector 27 which are the activated state detectors.

As shown in FIG. 5, the first pressure state detector 27 is electrically connected to a bending operation detector 30 provided in the control unit 9. The bending operation detector 30 is configured to perform a calculation in accordance with the activated state of each of the first press portions 22A to 22D detected by the first pressure sensor 26A and the first pressure state detector 27, and to detect the bending operation in the joystick 18A. The bending operation detector 30 is electrically connected to a controller 31 provided in the control unit 9. The whole endoscope system is controlled by the controller 31. The controller 31 is electrically connected to a drive command section 32 provided in the control unit 9.

The drive command section 32 is electrically connected to a motor 29 which is a drive member provided in the operation section body 10. The drive command section 32 configured to drive the motor 29 in accordance with the bending operation in the joystick 18A detected by the bending operation detector 30. One ends of wires 33 which are linear members are connected to the motor 29. The other ends of the wires 33 are connected to the bending section 7 through the flexible section 6. When the motor 29 is driven, the wires 33 move in the longitudinal directions. In response to the longitudinal movement of the wires 33, the bending section 7 performs the bending motion.

As shown in FIG. 5 and FIG. 6, when the first bending operation input unit 11A is attached to the operation section body 10, the second pressure sensor 26B of the pressure sensitive sheet 26 is pressed by the second press portion 23. When the other bending operation input units 11B to 11F are attached to the operation section body 10, the second pressure sensor 26B is also pressed by the second press portion 23. The shape of the second press portion 23 varies in accordance with the type of bending operation input unit 11A to 11F. The control method of the bending operation in a normal state is determined by the shape of the second press portion 23. That is, the second press portion 23 is a control method input section configured to input the control method of the bending operation in the normal state.

As shown in FIG. 5 and FIG. 6, the second pressure sensor 26B is electrically connected to a second pressure state detector 37 provided in the operation section body 10. The second pressure state detector 37 is configured to detect the pressure state of the second pressure sensor 26B of the pressure sensitive sheet 26. The shape of the second press portion 23 is detected from the pressure state of the second pressure sensor 26B. For example, the pressure state of the second pressure sensor 26B varies depending on whether the second press portion 23 is semicircular or prism-shaped. That is, the second press portion 23 is configured to presses the second pressure sensor 26B so that the pressure state of the second pressure sensor 26B varies in accordance with the type of bending operation input unit 11A to 11F. By detecting the shape of the second press portion 23, the control method of the bending operation in the normal state input by the second press portion 23 which is the control method input section is detected. That is, a bending control parameter used to determine the bending amount of the bending section 7 with respect to the bending operation in each of bending operation input units 11A to 11F is recorded in the controller 31 for each of bending operation input units 11A to 11F. From the shape of the second press portion 23, the second pressure state detector 37 is configured to detect the type of bending operation input unit 11A to 11F attached to the operation section body 10. The bending control parameter corresponding to the type of bending operation input unit 11A to 11F attached to the operation section body 10 is then selected. As described above, the second pressure sensor 26B and the second pressure state detector 37 serve as control method detectors configured to detect the control method of the bending operation in the normal state input by the second press portion 23 which is the control method input section.

Here, no electrical contact is provided between the second pressure sensor 26B and the second press portion 23. Therefore, the second press portion 23 which is the control method input section is electrically insulated from the second pressure sensor 26B and the second pressure state detector 37 which are the control method detectors.

As shown in FIG. 5, the second pressure state detector 37 is electrically connected to the controller 31 provided in the control unit 9. As described above, the controller 31 is electrically connected to the drive command section 32. The drive command section 32 is configured to drive the motor 29 in accordance with the control method of the bending operation in the normal state detected by the second pressure sensor 26B and the second pressure state detector 37. The operation portion body 10 is provided with a control method changing switch 39 which is electrically connected to the controller 31 of the control unit 9. The operator operates the control method changing switch 39 to change the control method of the bending operation from the control method in the normal state.

Now, the function of the endoscope 1 according to the present embodiment is described. In order to bend the bending section 7 of the endoscope 1, a proper type of bending operation input unit 11A to 11F is attached to the unit attachment/removal portion 15 of the operation section body 10 to suit each case and the preference of the operator. In this case, one of bending operation input units 11A to 11F is attached to the unit attachment/removal portion 15 of the operation section body 10 by the attraction between the first magnet 25A and the second magnet 25B.

When one of bending operation input units 11A to 11F is attached to the operation section body 10, the second pressure sensor 26B of the pressure sensitive sheet 26 is pressed by the second press portion 23. The shape of the second press portion 23 varies in accordance with the type of bending operation input unit 11A to 11F. In this case, the second pressure state detector 37 detects the pressure state of the second pressure sensor 26B of the pressure sensitive sheet 26. The shape of the second press portion 23 is detected from the pressure state of the second pressure sensor 26B. By detecting the shape of the second press portion 23, the control method of the bending operation in the normal state input by the second press portion 23, which is the control method input section, is detected. The operator can change the control method of the bending operation from the control method in the normal state by operating the control method changing switch 39 of the operation section body 10.

When the first bending operation input unit 11A is attached to the operation section body 10, the bending section 7 is bent by the operation in the joystick 18A. In response to the tilting motion of the joystick 18A, each of the first press portions 22A to 22D changes its activated state between the non-press state of not pressing the first pressure sensor 26A and the press state of pressing the first pressure sensor 26A. The first pressure state detector 27 then detects the pressure state of the first pressure sensor 26A of the pressure sensitive sheet 26. The activated state of each of the first press portions 22A to 22D is detected from the pressure state of the first pressure sensor 26A. The bending operation detector 30 then detects the bending operation in the joystick 18A in accordance with the activated state of each of the first press portions 22A to 22D detected by the first pressure sensor 26A and the first pressure state detector 27.

In accordance with the bending operation in the joystick 18A detected by the bending operation detector 30, the drive command section 32 drives the motor 29 by the control method in the normal state detected by the second pressure sensor 26B and the second pressure state detector 37 or by the control method changed by the operation in the control method changing switch 39. When the motor 29 is driven, the wires 33 move in the longitudinal directions. In response to the longitudinal movements of the wires 33, the bending section 7 performs the bending motion.

Thus, the endoscope 1 having the configuration described above provides the following advantageous effects. That is, in the endoscope 1, in order to bend the bending section 7, one of bending operation input units 11A to 11F is removably attached to the unit attachment/removal portion 15 of the operation section body 10 to perform the bending operation. Therefore, a proper type of bending operation input unit 11A to 11F can be used to suit each case and the preference of the operator.

Furthermore, in the endoscope 1, each of the first press portions 22A to 22D changes its activated state between the non-press state of not pressing the first pressure sensor 26A and the press state of pressing the first pressure sensor 26A in response to the operation in the bending operation input section (for example, the joystick 18A or the TACT switch [registered trademark] 18B) of each of bending operation input units 11A to 11F. The first pressure state detector 27 then detects the pressure state of the first pressure sensor 26A of the pressure sensitive sheet 26. The activated state of each of the first press portions 22A to 22D is detected from the pressure state of the first pressure sensor 26A. The bending operation detector 30 then detects the bending operation in the bending operation input section in accordance with the activated state of each of the first press portions 22A to 22D detected by the first pressure sensor 26A and the first pressure state detector 27. The bending operation in the bending operation input section is detected by such a configuration, so that it is not necessary to provide an electrical contact between the operation section body 10 and each of bending operation input units 11A to 11F removably attached to the operation section body 10, and the first press portions 22A to 22D are electrically insulated from the first pressure sensor 26A. Thus, the bending operation mechanism does not fail, for example, because of the smeared electrical contact between the operation section body 10 and each of bending operation input units 11A to 11F. Accordingly, the bending section 7 can be properly bent by the operation in the bending operation input section. As no electrical contact is provided between the operation section body 10 and each of bending operation input units 11A to 11F, the surface of the unit attachment/removal portion 15 of the operation section body 10 to be attached to or removed from each of bending operation input units 11A to 11F is formed into a flat shape. This makes it easier to wash the unit attachment/removal portion 15 of the operation section body 10 after the use of the endoscope 1.

Still further, when one of bending operation input units 11A to 11F is attached to the operation section body 10, the second pressure sensor 26B of the pressure sensitive sheet 26 is pressed by the second press portion 23. In this case, the second pressure state detector 37 detects the pressure state of the second pressure sensor 26B of the pressure sensitive sheet 26. The shape of the second press portion 23 is then detected from the pressure state of the second pressure sensor 26B. By detecting the shape of the second press portion 23, the control method of the bending operation in the normal state input by the second press portion 23, which is the control method input section, is detected. Such a configuration permits the bending operation in the normal state to be performed by the control method suited to the control method input section of each of bending operation input units 11A to 11F. The control method of the bending operation can be changed from the control method in the normal state to suit the preference of the operator by operating the control method changing switch 39 of the operation section body 10.

Still further, the control method of the bending operation in the normal state is detected by the configuration described above, so that it is not necessary to provide an electrical contact between the operation section body 10 and each of bending operation input units 11A to 11F that can be removably attached to the operation section body 10, and the second press portion 23 is electrically insulated from the second pressure sensor 26B. Thus, the mechanism configured to detect the control method of the bending operation in the normal state does not fail, for example, because of the smeared electrical contact between the operation section body 10 and each of bending operation input units 11A to 11F. Accordingly, the control method of the bending operation in the normal state can be properly detected. Moreover, as no electrical contact is provided between the operation section body 10 and each of bending operation input units 11A to 11F, the surface of the unit attachment/removal portion 15 of the operation section body 10 to be attached to or removed from each of bending operation input units 11A to 11F is formed into a flat shape. This makes it easier to wash the unit attachment/removal portion 15 of the operation section body 10 after the use of the endoscope 1.

(Modification of First Embodiment)

In the first embodiment, the shape of the second press portion 23 varies in accordance with the type of bending operation input unit 11A to 11F, and the control method of the bending operation in the normal state is determined by the shape of the second press portion 23. However, this is not a limitation. For example, the number or height of the second press portion 23 may vary in accordance with the type of bending operation input unit 11A to 11F. In this case, the control method of the bending operation in the normal state is determined, for example, by the number or height of the second press portion 23. That is, the second press portion 23 has only to be configured to press the second pressure sensor 26B so that the pressure state of the second pressure sensor 26B varies in accordance with the type of bending operation input unit 11A to 11F.

(Second Embodiment)

Now, a second embodiment of the present invention is described with reference to FIG. 7 to FIG. 9. The same parts as in the first embodiment and parts having the same functions are provided with the same reference sings and are not described. In the case described below, a second bending operation input unit 11B including a TACT switch (registered trademark) 18B as a bending operation input section is attached to an operation section body 10. However, the same applies to the cases where other bending operation input units 11A, and 11C to 11F are attached to the operation section body 10 as in the case where the second bending operation input unit 11B is attached to the operation section body 10.

FIG. 7 is a diagram showing an attachment/removal configuration between the operation section body 10 and the second bending operation input unit 11B. As shown in FIG. 7, a unit attachment/removal portion 15 of the operation section body 10 is provided with a depressed portion 41. The second bending operation input unit 11B is provided with a projecting portion 42 which can engage with the depressed portion 41. The projecting portion 42 engages with the depressed portion 41 so that the second bending operation input unit 11B is removably attached to the operation section body 10. At least part of the attachment/removal surface of the unit attachment/removal portion 15 of the operation section body 10 is formed to be transparent. Similarly, at least part of the attachment/removal surface of the second bending operation input unit 11B is formed to be transparent. Therefore, light is transmitted between the operation section body 10 and the second bending operation input unit 11B through the transparent part of the attachment/removal surface of the operation section body 10 and the transparent part of the attachment/removal surface of the second bending operation input unit 11B. The transparent part of the unit attachment/removal portion 15 and the transparent part of the second bending operation input unit 11B are made of a relatively rigid and transparent resin material such as polycarbonate. This prevents the second bending operation input unit 11B from being damaged during washing and during attachment/removal.

Figure 8:
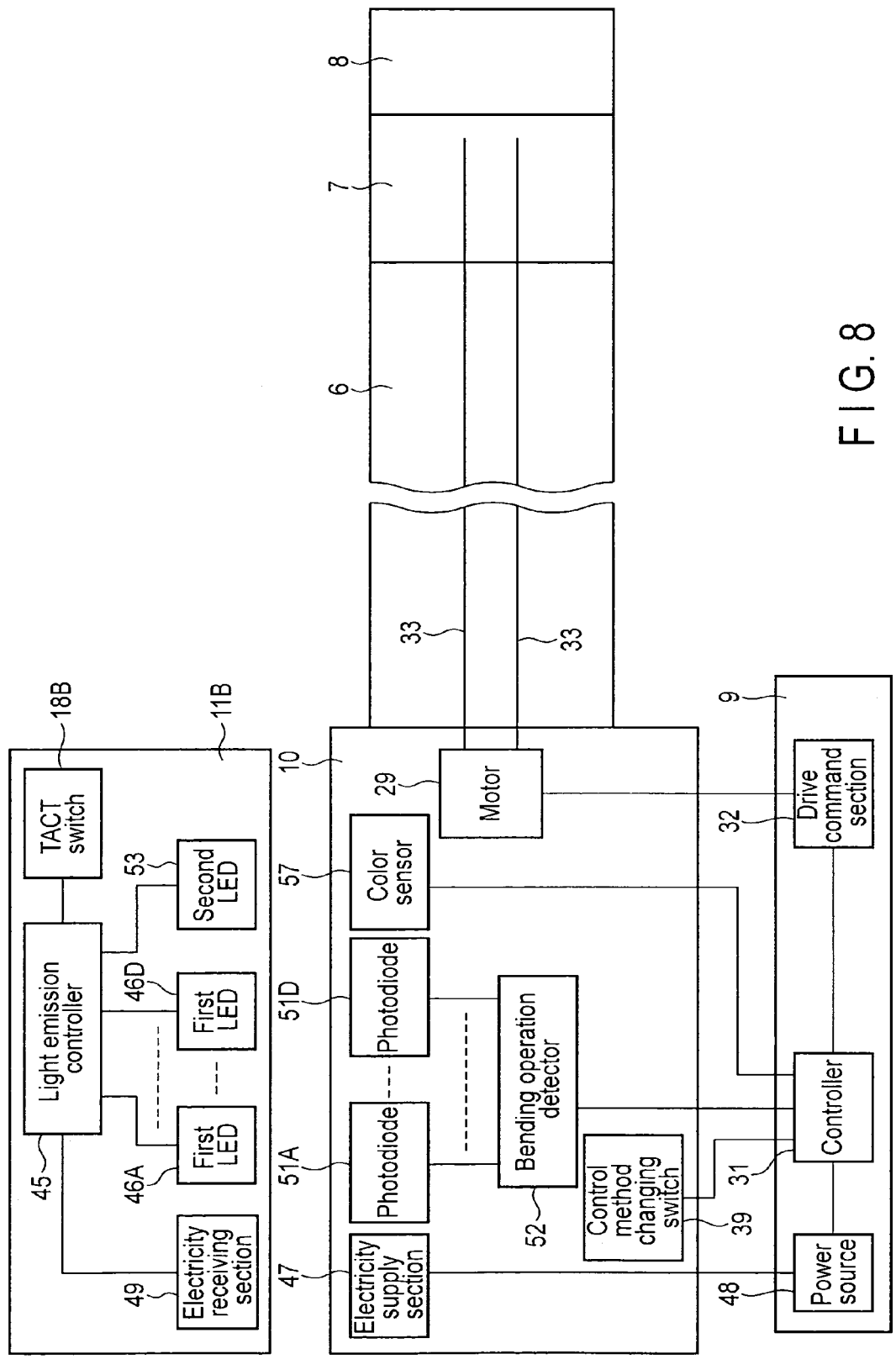
FIG. 8 is a block diagram showing a bending operation mechanism of the endoscope according to the second embodiment.

FIG. 8 is a diagram showing a bending operation mechanism of an endoscope 1. FIG. 9 is a diagram showing an attachment/removal portion between the operation section body 10 and the second bending operation input unit 11B in the endoscope 1. The TACT switch (registered trademark) 18B as the bending operation input section includes four buttons 43A to 43D (see FIG. 7). As shown in FIG. 9, each of buttons 43A to 43D is electrically connected to a light emission controller 45 provided in the second bending operation input unit 11B. The second bending operation input unit 11B includes four first LEDs 46A to 46D which are first light emitting components. Each of the first LEDs 46A to 46D is electrically connected to the light emission controller 45. In a neutral state in which none of buttons 43A to 43D are pressed, all the first LEDs 46A to 46D are extinguished. If one of buttons 43A to 43D of the TACT switch (registered trademark) 18B is pressed by the operator, one of the first LEDs 46A to 46D corresponding to the one of buttons 43A to 43D that is pressed is lit. For example, when button 43A is pressed, first LED 46A is lit. Each of the first LEDs 46A to 46D changes its activated state between extinguished state and lit state in response to the operation in the TACT switch (registered trademark) 18B. That is, each of the first LEDs 46A to 46D serves as an activated portion configured to change its activated state in response to the operation in the TACT switch (registered trademark) 18B which is the bending operation input section.

Figure 9:
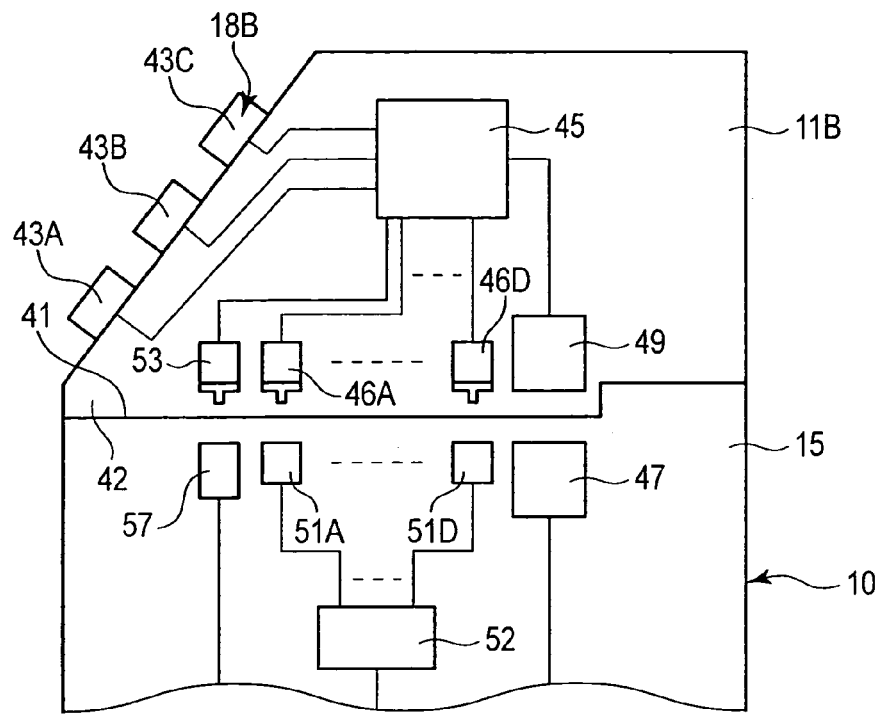
FIG. 9 is a schematic diagram showing an attachment/removal portion between the operation section body and the second bending operation input unit in the endoscope according to the second embodiment.

As shown in FIG. 8 and FIG. 9, the operation section body 10 includes an electricity supply section 47. The electricity supply section 47 is electrically connected to a power source 48 provided in the control unit 9. The second bending operation input unit 11B includes an electricity receiving section 49 which is supplied with electricity from the electricity supply section 47. The electricity receiving section 49 is electrically connected to the light emission controller 45. The light emission controller 45 uses the electricity supplied to the electricity receiving section 49 to light each of the first LEDs 46A to 46D. The electricity supply section 47 is electrically insulated from the electricity receiving section 49. Electricity supplied from the electricity supply section 47 to the electricity receiving section 49, for example, by magnetic induction or photovoltaic power generation. Thus, electricity is supplied from the electricity supply section 47 to the electricity receiving section 49 without providing an electrical contact between the unit attachment/removal portion 15 of the operation section body 10 and the second bending operation input unit 11B.

As shown in FIG. 8 and FIG. 9, the operation section body 10 includes four photodiodes 51A to 51D which are light receiving components. Each of photodiodes 51A to 51D receives light from the corresponding first LED 46A to 46D when any one of the first LEDs 46A to 46D is lit. For example, when first LED 46A is lit, photodiode 51A receives light from first LED 46A. The activated state of each of the first LEDs 46A to 46D is detected by whether each of photodiodes 51A to 51D receives light. As described above, photodiodes 51A to 51D serve as activated state detectors configured to detect the activated states of the first LEDs 46A to 46D which are the activated portions.

Here, no electrical contact is provided between photodiodes 51A to 51D and the first LEDs 46A to 46D. Therefore, the first LEDs 46A to 46D which are the activated portions are electrically insulated from photodiodes 51A to 51D which are the activated state detectors.

As shown in FIG. 8, each of photodiodes 51A to 51D is electrically connected to a bending operation detector 52 provided in the operation section body 10. The bending operation detector 52 is configured to perform a calculation in accordance with the activated state of each of the first LEDs 46A to 46D detected by corresponding one of photodiodes 51A to 51D, and to detect the bending operation in the TACT switch (registered trademark) 18B. The bending operation detector 52 is electrically connected to a controller 31 provided in the control unit 9. The controller 31 is electrically connected to a drive command section 32 provided in the control unit 9. The drive command section 32 is electrically connected to a motor 29 which is a drive member provided in the operation section body 10. The drive command section 32 is configured to drive the motor 29 in accordance with the bending operation in the TACT switch (registered trademark) 18B detected by the bending operation detector 52. One ends of wires 33 which are linear members are connected to the motor 29. The other ends of the wires 33 are connected to a bending section 7 through a flexible section 6. When the motor 29 is driven, the wires 33 move in the longitudinal directions. In response to the longitudinal movement of the wires 33, the bending section 7 performs the bending motion.

As shown in FIG. 8 and FIG. 9, the second bending operation input unit 11B includes a second LED 53 which is a second light emitting component electrically connected to the light emission controller 45. The light emission controller 45 is configured to light the second LED 53 by electricity supplied to the electricity receiving section 49. Each of the other bending operation input units 11A, and 11C to 11F also includes a second LED 53. The light color of the second LED 53 when lit varies in accordance with the type of bending operation input unit 11A to 11F. That is, the type of light of the second LED 53 varies in accordance with the type of bending operation input unit 11A to 11F. The control method of the bending operation in the normal state is determined by the light color of the second LED 53. That is, the second LED 53 is a control method input section configured to input the control method of the bending operation in the normal state.

As shown in FIG. 8 and FIG. 9, the operation section body 10 includes a color sensor 57. The color sensor 57 is configured to receive light from the second LED 53, and to detect the color of the received light. That is, the color sensor 57 is a light type detector configured to detect the type of light received from the second LED. By detecting the color of the light from the second LED 53, the control method of the bending operation in the normal state input by the second LED 53, which is the control method input section, is detected. As described above, the color sensor 57 serves as a control method detector configured to detect the control method of the bending operation in the normal state input by the second LED 53 which is the control method input section.

Here, no electrical contact is provided between the color sensor 57 and the second LED 53. Therefore, the second LED 53 which is the control method input section is electrically insulated from the color sensor 57 which is the control method detector.

As shown in FIG. 8, the color sensor 57 is electrically connected to the controller 31 provided in the control unit 9. As described above, the controller 31 is electrically connected to the drive command section 32. The drive command section 32 is configured to drive the motor 29 in accordance with the control method of the bending operation in the normal state detected by the color sensor 57. As in the first embodiment, the operator operates the control method changing switch 39 to change the control method of the bending operation from the control method in the normal state.

Now, the function of the endoscope 1 according to the present embodiment is described. In order to bend the bending section 7 of the endoscope 1, a proper type of bending operation input unit 11A to 11F is attached to the unit attachment/removal portion 15 of the operation section body 10 to suit each case and the preference of the operator. At the same time, one of bending operation input units 11A to 11F is attached to the unit attachment/removal portion 15 of the operation section body 10 by the engagement of the projecting portion 42 with the depressed portion 41.

When one of bending operation input units 11A to 11F is attached to the operation section body 10, light from the second LED 53 is received by the color sensor 57. The light color of the second LED 53 varies in accordance with the type of bending operation input unit 11A to 11F. In this case, the color sensor 57, which is a light color detector, detects the color of the received light. By detecting the color of the light received by the color sensor 57, the control method of the bending operation in the normal state input by the second LED 53, which is the control method input section, is detected. The operator can change the control method of the bending operation from the control method in the normal state by operating the control method changing switch 39 of the operation section body 10.

When the second bending operation input unit 11B is attached to the operation section body 10, the bending section 7 is bent by the operation in the TACT switch (registered trademark) 18B. In response to the press state of each of buttons 43A to 43D of the TACT switch (registered trademark) 18B, each of the first LEDs 46A to 46D changes its activated state between extinguished state and lit state. When any one of the first LEDs 46A to 46D is lit, each of photodiodes 51A to 51D receives light from the corresponding first LEDs 46A to 46D. The activated state of each of the first LEDs 46A to 46D is detected by whether corresponding photodiode 51A to 51D receives light. The bending operation detector 52 then detects the bending operation in the TACT switch (registered trademark) 18B in accordance with the activated state of each of the first LEDs 46A to 46D detected by photodiodes 51A to 51D.

In accordance with the bending operation in the TACT switch (registered trademark) 18B detected by the bending operation detector 52, the drive command section 32 drives the motor 29 by the control method in the normal state detected by the color sensor 57 or by the control method changed by the operation in the control method changing switch 39. When the motor 29 is driven, the wires 33 move in the longitudinal directions. In response to the longitudinal movement of the wires 33, the bending section 7 performs the bending motion.

Thus, the endoscope 1 having the configuration described above provides the following advantageous effects. That is, in the endoscope 1, in order to bend the bending section 7, one of bending operation input units 11A to 11F is removably attached to the unit attachment/removal portion 15 of the operation section body 10 to perform the bending operation. Therefore, a proper type of bending operation input unit 11A to 11F can be used to suit each case and the preference of the operator.

Furthermore, in the endoscope 1, each of the first LEDs 46A to 46D changes its activated state between extinguished state and lit state in response to the operation in the bending operation input section (for example, the joystick 18A or the TACT switch [registered trademark] 18B) of each of bending operation input units 11A to 11F. Each of photodiodes 51A to 51D then receives light from the corresponding first LED 46A to 46D when any one of the first LEDs 46A to 46D is lit. The activated state of each of the first LEDs 46A to 46D is detected by whether corresponding one of photodiodes 51A to 51D receives light. The bending operation detector 52 then detects the bending operation in the bending operation input section in accordance with the activated state of each of the first LEDs 46A to 46D detected by corresponding one of photodiodes 51A to 51D. The bending operation in the bending operation input section is detected by such a configuration, so that it is not necessary to provide an electrical contact between the operation section body 10 and each of bending operation input units 11A to 11F removably attached to the operation section body 10, and the first LEDs 46A to 46D are electrically insulated from photodiodes 51A to 51D. Thus, the bending operation mechanism does not fail, for example, because of the smeared electrical contact between the operation section body 10 and each of bending operation input units 11A to 11F. Accordingly, the bending section 7 can be properly bent by the operation in the bending operation input section. As no electrical contact is provided between the operation section body 10 and each of bending operation input units 11A to 11F, the surface of the unit attachment/removal portion 15 of the operation section body 10 to be attached to or removed from each of bending operation input units 11A to 11F is formed into a flat shape. This makes it easier to wash the unit attachment/removal portion 15 of the operation section body 10 after the use of the endoscope 1.

Still further, when one of bending operation input units 11A to 11F is attached to the operation section body 10, the color sensor 57 receives light from the second LED 53. In this case, the color sensor 57 detects the color of the received light. By detecting the color of the light received by the color sensor 57, the control method of the bending operation in the normal state input by the second LED 53, which is the control method input section, is detected. Such a configuration permits the bending operation in the normal state to be performed by the control method suited to the control method input section of each of bending operation input units 11A to 11F. The control method of the bending operation can be changed from the control method in the normal state to suit the preference of the operator by operating the control method changing switch 39 of the operation section body 10.

Still further, the control method of the bending operation in the normal state is detected by the configuration described above, so that it is not necessary to provide an electrical contact between the operation section body 10 and each of bending operation input units 11A to 11F that can be removably attached to the operation section body 10, and the second LED 53 is electrically insulated from the color sensor 57. Thus, the mechanism configured to detect the control method of the bending operation in the normal state does not fail, for example, because of the smeared electrical contact between the operation section body 10 and each of bending operation input units 11A to 11F. Accordingly, the control method of the bending operation in the normal state can be properly detected. Moreover, as no electrical contact is provided between the operation section body 10 and each of bending operation input units 11A to 11F, the surface of the unit attachment/removal portion 15 of the operation section body 10 to be attached to or removed from each of bending operation input units 11A to 11F is formed into a flat shape. This makes it easier to wash the unit attachment/removal portion 15 of the operation section body 10 after the use of the endoscope 1.

Still further, in the endoscope 1, electricity is supplied to the electricity receiving section 49 from the electricity supply section 47 electrically connected to the power source 48. The light emission controller 45 lights the first LEDs 46A to 46D and the second LED 53 by electricity supplied to the electricity receiving section 49. The electricity supply section 47 is electrically insulated from the electricity receiving section 49. Electricity supplied from the electricity supply section 47 to the electricity receiving section 49, for example, by magnetic induction or photovoltaic power generation. Thus, electricity can be supplied from the electricity supply section 47 to the electricity receiving section 49 without providing an electrical contact between the unit attachment/removal portion 15 of the operation section body 10 and the second bending operation input unit 11B.

Still further, for example, in the first embodiment, the positions and shapes of the first press portions 22A to 22D need to be set so that each of the first press portions 22A to 22D is located to be able to press the first pressure sensor 26A of the pressure sensitive sheet 26 of the operation section body 10. The bending operation input section, for example, the joystick 18A changes the activated state of each of the first press portions 22A to 22D by a dynamic configuration. Thus, if the positions and shapes of the first press portions 22A to 22D are limited, the position and shape of the bending operation input section are also limited. In the meantime, according to the present embodiment, the activated state of each of the first LEDs 46A to 46D changes between extinguished state and lit state in response to the operation in the bending operation input section. That is, the activated state of each of the first LEDs 46A to 46D is not changed by the dynamic configuration. Therefore, as compared with the first embodiment, the degree of freedom is higher in the positions of the first LEDs 46A to 46D and in the position and shape of the bending operation input section. As a result, the position and shape of the bending operation input section can be set so that the operator can easily operate the bending operation input section.

(Modification of Second Embodiment)

In the second embodiment, the light color of the second LED 53 varies in accordance with the type of bending operation input unit 11A to 11F, and the control method of the bending operation in the normal state is determined by the light color of the second LED 53. However, this is not a limitation. For example, the light emission period, luminance, or number of the second LED 53 may vary in accordance with the type of bending operation input unit 11A to 11F. In this case, the control method of the bending operation in the normal state is determined, for example, by the light emission period, luminance, or number of the second LED 53. That is, the type of light of the second LED 53 has only to be configured to vary in accordance with the type of bending operation input unit 11A to 11F. In this case, the operation section body 10 includes a light type detector configured to detect the type of light received from the second LED 53.

(Other Modifications)

In the first embodiment, the activated states of the first press portions 22A to 22D which are the activated portions are detected from the pressure state of the first pressure sensor 26A, and the bending operation in the bending operation input section is detected. In the second embodiment, the activated states of the first LEDs 46A to 46D which are the activated portions are detected by photodiodes 51A to 51D, and the bending operation in the bending operation input section is detected. However, the configuration which detects the bending operation in the bending operation input section is not limited to the configurations in the embodiments described above.

Figure 10:
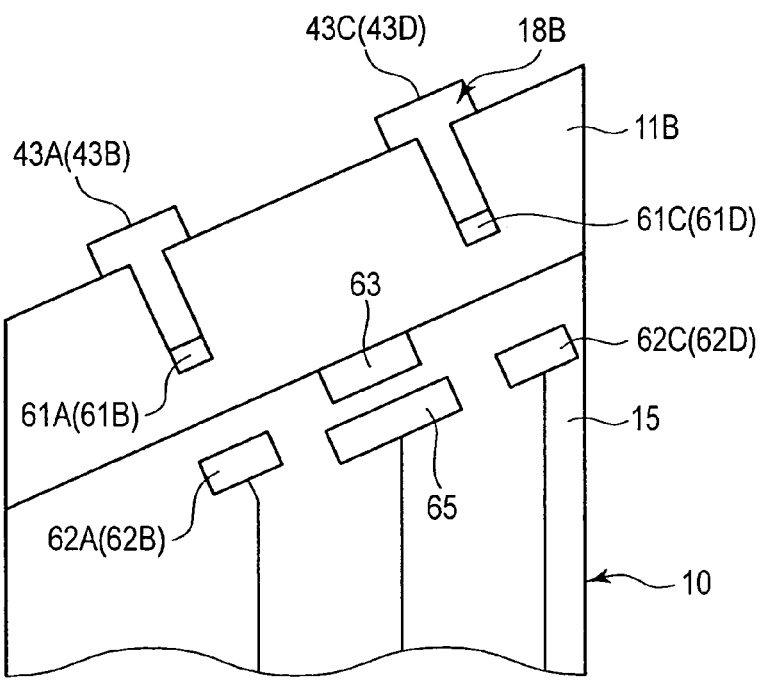
FIG. 10 is a schematic diagram showing an attachment/removal portion between an operation section body and a second bending operation input unit in an endoscope according to a first modification of the first embodiment and the second embodiment.

FIG. 10 is a diagram showing an attachment/removal portion between an operation section body 10 and a second bending operation input unit 11B according to a first modification. As shown in FIG. 10, the second bending operation input unit 11B includes four first magnets 61A to 61D. Each of the first magnets 61A to 61D is attached to corresponding button 43A to 43D of a TACT switch (registered trademark) 18B. When any one of buttons 43A to 43D is pressed by the bending operation in the TACT switch (registered trademark) 18B, each of the first magnets 61A to 61D moves together with the corresponding button 43A to 43D. For example, when button 43A is pressed, first magnet 61A moves together with button 43A. Each of the first magnets 61A to 61D moves and thereby changes its activated state between a closest state closest to the operation section body 10 and a farthest state farthest from the operation section body 10. That is, each of the first magnets 61A to 61D serves as an activated portion configured to change its activated state in response to the bending operation in the TACT switch (registered trademark) 18B.

Four first magnetic sensors 62A to 62D are fixedly provided in the operation section body 10. Each of the first magnetic sensors 62A to 62D is configured to detect the intensity of a magnetic field formed by the corresponding first magnet 61A to 61D. For example, the first magnetic sensor 62A detects the intensity of the magnetic field formed by the first magnet 61A. As each of the first magnets 61A to 61D moves, the intensity of the magnetic field detected by each of the first magnetic sensors 62A to 62D changes in response to the change of the activated state of the corresponding first magnet 61A to 61D. Each of the first magnetic sensors 62A to 62D detects the intensity of the magnetic field formed by the corresponding first magnet 61A to 61D, so that the activated state of each of the first magnets 61A to 61D is detected. That is, the first magnetic sensors 62A to 62D are activated state detectors configured to detect the activated states of the first magnets 61A to 61D which are activated portions. In accordance with the activated states of the first magnets 61A to 61D, the bending operation detector 30 is configured to detect the bending operation in the TACT switch (registered trademark) 18B. Here, the first magnets 61A to 61D, which are activated portions, are electrically insulated from the first magnetic sensors 62A to 62D, which are activated state detectors.

As described above, according to the first modification, the endoscope 1 has only to include the activated portion which is provided in each of bending operation input units 11A to 11F, and which is configured to change its activated state in response to the bending operation in the bending operation input section, and the activated state detector which is provided in the operation section body 10 to be electrically insulated from the activated portion, and which is configured to detect the activated state of the activated portion.

In the first embodiment, the control method of the bending operation in the normal state input by the second press portion 23, which is the control method input section, is detected from the pressure state of the second pressure sensor 26B. In the second embodiment, the control method of the bending operation in the normal state input by the second LED 53, which is the control method input section, is detected from the type of light received by the color sensor 57. However, the configuration which is detects the control method of the bending operation in the normal state is not limited to the configurations in the embodiments described above.

As shown in FIG. 10, the second bending operation input unit 11B according to the first modification includes a second magnet 63. Each of the other bending operation input units 11A, and 11C to 11F also includes a second magnet 63. The intensity of a magnetic field formed by the second magnet 63 varies in accordance with the type of bending operation input unit 11A to 11F. The control method of the bending operation in the normal state is determined by the intensity of the magnetic field formed by the second magnet 63. That is, the second magnet 63 is a control method input section configured to input the control method of the bending operation in the normal state.

The operation section body 10 includes a second magnetic sensor 65 configured to detect the intensity of the magnetic field formed by the second magnet 63. The control method of the bending operation in the normal state input by the second magnet 63, which is the control method input section, is detected by the intensity of the magnetic field detected by the second magnetic sensor 65. As described above, the second magnetic sensor 65 serves as a control method detector configured to detect the control method of the bending operation in the normal state input by the second magnet 63 which is the control method input section. Here, the second magnet 63, which is the control method input section, is electrically insulated from the second magnetic sensor 65, which is the control method detector.

As described above, according to the first modification, the endoscope 1 has only to include the control method input section which is provided in each of bending operation input units 11A to 11F, and which is configured to input the control method of the bending operation, and the control method detector which is provided in the operation section body 10 to be electrically insulated from the control method input section, and which is configured to detect the control method of the bending operation input by the control method input section.

FIG. 11 is a diagram showing an operation section 3 of an endoscope 1 according to a second modification of the above-described embodiments. As shown in FIG. 11, according to the present modification, an input section conversion unit 70 is removably attached to a first bending operation input unit 11A which includes a joystick 18A as a bending operation input section. The input section conversion unit 70 includes a pointing device 71 as a bending operation input section. When the input section conversion unit 70 is attached to the first bending operation input unit 11A, the operator performs the bending operation of a bending section 7 by using the pointing device 71.

FIG. 12 is a diagram showing an attachment/removal portion between the first bending operation input unit 11A and the input section conversion unit 70. As shown in FIG. 12, the joystick 18A includes a ball 72 and a lever 73. The input section conversion unit 70 includes an exterior case 75. The pointing device 71 is attached to the exterior case 75 via a spring 76. The pointing device 71 is provided with a valley 77 which can engage with the ball 72 of the joystick 18A. The exterior case 75 is provided with a lock portion 79 which is locked by the first bending operation input unit 11A when the input section conversion unit 70 is attached to the first bending operation input unit 11A. The valley 77 of the pointing device 71 engages with the ball 72, and the lock portion 79 of the exterior case 75 is locked by the first bending operation input unit 11A, and the input section conversion unit 70 is thereby attached to the first bending operation input unit 11A.

The configuration described above permits the bending operation input section to be converted from the joystick 18A to the pointing device 71 without changing the first bending operation input unit 11A attached to the operation section body 10.

FIG. 13 is a diagram showing a first bending operation input unit 11A according to a third modification of the above-described embodiments. As shown in FIG. 13, a joystick 18A includes a ball 72 and a lever 73. The first bending operation input unit 11A has an attachment surface 80 to which the joystick 18A is attached. A knob 81 is attached to the ball 72 rotatably relative to the ball 72. An upper surface 81A of the knob 81 is formed into a shape that easily fits the fingertip. In a neutral state in which the joystick 18A is not tilted, a lower surface 81B of the knob 81 is parallel to the attachment surface 80 of the first bending operation input unit 11A. In the neutral state of the joystick 18A, the angle between the lever 73 and the attachment surface 80 of the first bending operation input unit 11A is 90°.

In order to perform the bending operation, the joystick 18A is tilted from the neutral state shown in FIG. 13, for example, to the state shown in FIG. 14. In this case, the angle between the lever 73 and the attachment surface 80 of the first bending operation input unit 11A is θ. The angle θ is smaller as the tilt amount of the joystick 18A is greater.

Here, when the knob 81 is fixedly attached to the ball 72 of the joystick 18A, the knob 81 does not rotate relative to the ball 72. Therefore, when the joystick 18A is tilted, the lower surface 81B of the knob 81 is not parallel to the attachment surface 80 of the first bending operation input unit 11A (a dotted line in FIG. 14). Thus, the finger does not easily fit the upper surface 81A of the knob 81.

In contrast, according to the present modification, the knob 81 is rotatably attached to the ball 72 of the joystick 18A. Therefore, when the joystick 18A is tilted, the knob 81 rotates relative to the ball 72 in a direction opposite to the tilting direction of the joystick 18A. Owing to the rotation of the knob 81, the lower surface 81B of the knob 81 is located parallel to the attachment surface 80 of the first bending operation input unit 11A (a solid line in FIG. 14) even when the joystick 18A is tilted. Thus, the finger easily fits the upper surface 81A of the knob 81 even when the joystick 18A is tilted. As the finger easily fits the upper surface 81A of the knob 81, the operator can properly apply force to the joystick 18A even when the joystick 18A is tilted. As a result, the operator can stably perform the bending operation, and the operability in the bending operation is improved.

FIG. 15 is a diagram showing a first bending operation input unit 11A according to a fourth modification of the above-described embodiments. As shown in FIG. 15, in the first bending operation input unit 11A according to the present modification, a leaf spring 83 is attached to a lower surface 81B of a knob 81 similar to the knob 81 according to the third modification. In the present modification, the configuration is similar to that according to the third modification except that the leaf spring 83 is provided.

In the present modification, the leaf spring 83 is provided, so that elastic force acts on a joystick 18A from the leaf spring 83 if the finger is released from the knob 81 while the joystick 18A is tilted. The joystick 18A is brought back to the neutral state by the elastic force from the leaf spring 83. Such a configuration allows the joystick 18A to be always held in the neutral state when the finger is released from an upper surface 81A of the knob 81. As a result, the operability in the bending operation is improved.

In the embodiments described above, the bending section 7 is bent in four directions including the upward/downward (UD) directions and leftward/rightward (LR) directions. However, the above-described configuration which detects the bending operation in the bending operation input section is also applicable when the bending section 7 is bent in two directions including the upward/downward directions or leftward/rightward directions. Similarly, the above-described configuration which detects the control method of the bending operation in the normal state is also applicable when the bending section 7 is bent in two directions including the upward/downward directions or leftward/rightward directions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion section which includes a bending section configured to perform a bending motion, and which extends in longitudinal directions;
an operation section body provided to a proximal direction side of the insertion section;
various types of bending operation input units, each of which includes a bending operation input section configured to input a bending operation to bend the bending section, and one of which is removably attached to the operation section body selectively;
activated portions each of which is provided in corresponding one of the bending operation input units, and each of which is configured to change its activated state in response to an input state of the bending operation by the bending operation input section provided in the corresponding one of the bending operation input units;
an activated state detector which is provided in the operation section body, and which is configured to detect the activated state of the activated portion of attached one of the bending operation input units in a state that the attached one of the bending operation input units is attached to the operation section body, the activated state detector being electrically insulated from the activated portion of the attached one of the bending operation input units;
control method input sections each of which is provided in corresponding one of the bending operation input units, and each of which is configured to input a type of the corresponding one of the bending operation input units in a state that the corresponding one of the bending operation input units is attached to the operation section body, wherein the control method input sections and the operation section body are separable;
a control method detector which is provided in the operation section body, and which is configured to detect a type of the attached one of the bending operation input units in the state that the attached one of the bending operation input units is attached to the operation section body, the control method detector being electrically insulated from the control method input section of the attached one of the bending operation input units, and the control method detector being configured to select a bending control parameter, by which a relationship between an input value of the bending operation and a bending amount of the bending section is determined, in accordance with the type of the attached one of the bending operation input units and thereby configured to detect a control method of the bending operation corresponding to the selected bending control parameter; and
a drive source which is provided in the operation section body, and which is configured to be driven in accordance with the control method detected by the control method detector and the activated state detected by the activated state detector, the drive source being configured to be driven by an electric power to cause a driving force of bending the bending section.

2. The endoscope according to claim 1, further comprising a bending operation detector configured to detect the bending operation by the bending operation input section of the attached one of the bending operation input units in accordance with the activated state of the activated portion of the attached one of the bending operation input units detected by the activated state detector, wherein the drive source is configured to be driven in accordance with the bending operation detected by the bending operation detector.

3. The endoscope according to claim 1, wherein the control method detector includes a pressure sensor, and a pressure state detector configured to detect a pressure state of the pressure sensor, each of the control method input sections includes a press portion which is configured to press the pressure sensor while the corresponding one the bending operation input units is attached to the operation section body, and the pressure state of the pressure sensor varies in accordance with the type of the attached one of the bending operation input units.

4. The endoscope according to claim 1, wherein the activated state detector includes a pressure sensor, and a pressure state detector configured to detect a pressure state of the pressure state, and each of the activated portions includes a press portion which is configured to change its activated state between a non-press state of not pressing the pressure sensor and a press state of pressing the pressure sensor in response to the bending operation by the bending operation input section of the attached one of the bending operation input units.

5. The endoscope according to claim 1, wherein the control method input section includes a light emitting component configured to vary in a type of light in accordance with a type of bending operation input unit, and the control method detector includes a light type detector which is configured to receive light from the light emitting component, and which is configured to detect the type of received light.

6. The endoscope according to claim 1, further comprising a linear member which is extended inside the insertion section, and which is configured to move in the longitudinal directions so as to bend the bending section when the driving force is transmitted from the drive source.

* * * * *